United States Patent [19]
Nycz et al.

[11] Patent Number: 5,723,296
[45] Date of Patent: Mar. 3, 1998

[54] AMPLIFICATION AND DETECTION OF MYCOBACTERIAL DNA K NUCLEIC ACIDS

[75] Inventors: Colleen Marie Nycz, Raleigh; James G. Nadeau, Chapel Hill; Patricia Brinkley Scott, Apex, all of N.C.; Daryl Dee Shank, BelAir, Md.; Patricia Anne Spears, Raleigh, N.C.

[73] Assignee: Becton, Dickinson and Company, Franklin Lakes, N.J.

[21] Appl. No.: 644,729

[22] Filed: May 10, 1996

Related U.S. Application Data

[63] Continuation of Ser. No. 347,551, Nov. 30, 1994, abandoned.

[51] Int. Cl.[6] .............. C12Q 1/68; C12Q 1/70; C12P 19/34; C07H 21/04
[52] U.S. Cl. .............. 435/6; 435/912; 536/243; 536/24.31; 536/24.32; 536/24.33
[58] Field of Search .............. 435/5, 6, 91.1, 435/91.2; 536/24.3, 24.31, 24.32, 24.33, 22.1, 23.1

[56] References Cited

U.S. PATENT DOCUMENTS

| | | | |
|---|---|---|---|
| 4,486,539 | 12/1984 | Ranki | 436/504 |
| 4,725,537 | 2/1988 | Fritsch | 435/6 |
| 5,232,829 | 8/1993 | Longiaru | 435/6 |
| 5,314,801 | 5/1994 | Nycz | 435/6 |
| 5,348,853 | 9/1994 | Wang | 435/6 |
| 5,352,580 | 10/1994 | Spears | 435/6 |
| 5,387,510 | 2/1995 | Wu | 435/91.2 |

FOREIGN PATENT DOCUMENTS

| | | |
|---|---|---|
| 0 304 184 A1 | 2/1989 | European Pat. Off. . |
| 461045-A1 | 12/1991 | European Pat. Off. . |
| 0 528 306 A2 | 8/1992 | European Pat. Off. . |
| 69375-A2 | 10/1994 | European Pat. Off. . |
| WI 87/03911 | 7/1987 | WIPO . |

OTHER PUBLICATIONS

Kawaguchi et al. "A non–radioactive method for the detection of a common mutant allele of aldehyde dehydrogenase 2". 1992. Mol. Cell. Probes 6:349–352.

Spargo et al. "Chemiluminescent detection of strand displacement amplified DNA from species comprising the Mycobacterium tuberculosis complex". 1993. Mol. Cell. Probes 7:395–404.

Shank et al. "Strand Displacement Amplification (SDA) of Mycobacterial genus specific sequences from the gene encoding for the 70K heat shock protein". 1993. Abst. Gen. Meet. Am. Soc. Microbiol. 93:175(U-39).

Little et al. "Nucleotide sequence and strand displacement amplification of the 70K protein gene from mycobacteria". 1994. Mol. Cell. Probes 8:375–384.

Walker et al. "Strand displacement amplification–an isothermal, in vitro DNA amplification technique". 1992. Nuc. Acids Res. 20:1691–1696.

Gibbs et al. "Detection of single DNA base differences by competitive oligonucleotide priming". 1989. Nuc. Acids Res. 17:2437–2448.

Complete Nucleotide Sequence of a Gene Encoding the 70 KD Heat Shock Protein of Mycobacterium Paratuberculosis, K. Stevenson, et al., Nucleic Acids Research, vol. 19, No. 16, 4552 (1991).

Nucleotide Sequence and Secondary Structures of Precursor 16S RRNA of Slow–Growing Mycobacteria, Y. Ji et al., Microbiology, 1994,140,123–132.

Sequence–Based Differentiation of strains in the Mycobacterium Avium Complex, J. of Bacteriology, 1993, vol. 175, No. 10, 2818–2825.

Detection and Identification of Mycobacteria by Amplification of RRNA, B. Boddinghaus, et al., J. of Clinical Microbiology, vol. 28, No. 8, 1990, 1751–1759.

Specific Detection of Mycobacterium Tuberculosis Complex Strains by Polymerase Chain Reaction, P. Hermans, et al., J. of Clinical Microbiology, vol. 28, No. 6, 1990, 1204–1213.

Homology of the 70–Kilodalton Antigens from Mycobacterium Leprae and Mycobacterim Bovis with the Mycobacterium Tuberculosis 71–Kildalton Antigen and with the Conserved Heat Shock Protein 70 of Eucaryotes, R. Garsia, et al., Infection and immunity, vol. 57, No. 1, 1989, 204–212.

Sequence and Immunogenicity of the 70–KDA Heat Shock Protein of Mycobacterium Laprae K. McKenzie, et al., J. of Immunology, vol. 147, No. 1, 1991, 312–319.

Cloning of the HSP70 Gene from Halobacterium Marismortu: Relatedness of archaebacterial HSP70 to its Eubacterial Homologs and a Model for the Evolution of the HSP70 Gene, R. Gupta, et al., J. Bacteriology, vol. 174, No. 14, 1992, 4594–4605.

A Gene from Mycobacterium Tuberculosis which is Homologous to the DNAJ Heat Shock Protein of E. Coli, R. Lathigra, et al., vol. 16, No. 4, 1988, 1636.

*Primary Examiner*—W. Gary Jones
*Assistant Examiner*—Jeffrey Fredman
*Attorney, Agent, or Firm*—Donna R. Fugit

[57] ABSTRACT

Methods for identification or detection of a species of an organism or a group of related species of an organism by species non-specific amplification of a target sequence followed by species- or group-specific detection of the amplification products. Also provided are a target sequence which is amplifiable in multiple species of mycobacteria using a single pair of amplification primers and species- and group-specific detector probes for hybridization to the assay regioin of the amplified target. Blocking oligonucleotides are employed to allow discrimination among species in which the amplified target sequences are sufficiently similar that they cross-hybridize to an assay probe.

10 Claims, 1 Drawing Sheet

FIG-1

AMPLIFICATION AND DETECTION OF MYCOBACTERIAL DNA K NUCLEIC ACIDS

This application is a continuation of application Ser. No. 08/347,551, filed Nov. 30, 1994, now abandoned.

FIELD OF THE INVENTION

The present invention relates to amplification and detection of target nucleic acid sequences. In particular, the invention relates to amplification and detection of target nucleic acid sequences in Mycobacteria.

BACKGROUND OF THE INVENTION

The Mycobacteria are a genus of bacteria which are acid-fist, non-motile, gram-positive rods. The genus comprises several species which include, but are not limited to, *Mycobacterium africanum, M. avium, M. bovis, M. bovis-BCG, M. chelonae, M. fortuitum, M. gordonae, M. intracellulare, M. kansasii, M. microti, M. scrofulaceum, M. paratuberculosis* and *M. tuberculosis*. Certain of these organisms are the causative agents of disease. For the first time since 1953, cases of mycobacterial infections are increasing in the United States. Although tuberculosis is of particular concern, other mycobacterial infections are also increasing as a result of an increase in the number of immune compromised patients. Many of these new cases are related to the AIDS epidemic, which provides an immune compromised population which is particularly susceptible to infection by Mycobacteria. *Mycobacterium avium, Mycobacterium kansasii* and other non-tuberculosis mycobacteria are found as opportunistic pathogens in HIV infected and other immune compromised patients. *M. avium* and *M. intracellulare* are members of the *Mycobacterium avium* complex (MAC). These species have become important in recent years because of the high prevalence of disseminated MAC infection in AIDS patients.

At the present time the diagnosis of mycobacterial infections is dependent on acid-fast staining and cultivation of the organism, followed by biochemical assays. These procedures are time-consuming, and a typical diagnosis using conventional culture methods can take as long as six weeks. Automated culturing systems such as the BACTEC™ system (Becton Dickinson Microbiology Systems, Sparks, Md.) can decrease the time for diagnosis to one to two weeks. However, there is still a need to reduce the time required for diagnosing Mycobacterial infections to less than a week, preferably to about one day. Nucleic acid amplification is a powerful technology which allows rapid detection of specific target sequences. It is therefore a promising technology for rapid detection and identification of Mycobacteria. Examples of nucleic acid amplification technologies known in the art are Polymerase Chain Reaction (PCR: U.S. Pat. Nos. 4,683,195; 4,683,202; 4,800,159; 4,965,188), Strand Displacement Amplification (SDA) (G. Walker, et al. 1992. *Proc. Nat. Acad. Sci. USA* 89, 392–396; G. Walker, et al. 1992. *Nucl. Acids Res.* 20, 1691–1696; U.S. Pat. No. 5,270,184 which is hereby incorporated by reference), nucleic acid sequence based amplification (NASBA: U.S. Pat. No. 5,130,238 to Cangene), transcription based amplification (D. Kwoh, et al. 1989. *Proc. Nat. Acad. Sci. USA* 86, 1173–1177), self-sustained sequence replication (3SR: J. Guatelli, et al. 1990. *Proc. Nat. Acad. Sci. USA* 87, 1874–1878) and the Qβ replicase system (P. Lizardi, et al. 1988. *BioTechnology* 6, 1197–1202).

Isothermal amplification methods such as SDA and 3SR have particular advantages in diagnostics, as they do not require the high/low temperature cycling characteristic of methods such as PCR. They are therefore simpler protocols and require less specialized equipment to perform. However, for any nucleic acid amplification method a target sequence which can be amplified with the desired type and degree of specificity must be identified before the technology can be applied. The sequence of a selected target may not necessarily allow design of appropriate amplification primers for the selected amplification method and may not necessarily be amplified and detected with a degree of sensitivity and specificity suitable for diagnosis. European Patent Application 0 528 306 describes PCR amplification of a target sequence in the 16S ribosomal RNA gene of Mycobacteria using amplification primers directed to conserved regions of the gene. The amplification product, which is approximately 583 base-pairs in length, contains conserved sequence regions which hybridize to genus-specific probes and variable regions which can be used to identify species using species-specific probes. While the assay system described in EPO 0 528 306 is based on species non-specific amplification followed by species-specific detection of the amplification products, it is significant that the amplification product produced is very large. The larger the target sequence being amplified, the more likely it is that the amplification product will contain regions with sufficient sequence variation to allow the design of a variety of non-cross-hybridizing, species-specific probes. Amplification methods such as SDA at this time are not capable of amplifying targets as large as those amplifiable by PCR. Small target sequences severely restrict the ability to design non-cross-hybridizing, species-specific probes for a given target because there is less sequence available in the amplification product for probe design. Clearly, in certain cases it may not be possible to design non-cross-hybridizing species-specific probes even when a target sequence is large. However, The problem of developing species-specific hybridization systems is particularly acute when small target sequences are being detected. The problem is compounded when the selection of the target is further restricted by the requirement for sequences flanking a variable assay region which are not only close enough together for amplification but which also are highly conserved among species, thereby allowing species non-specific amplification of the assay region prior to species-, complex- or group-specific detection.

The heat shock proteins are a family of proteins which are expressed in elevated amounts when an organism is challenged by an increase in temperature. The heat shock proteins are highly conserved (R. J. Garcia, et al. 1989. *Infection and Immunity* 57, 204–212; R. S. Gupta, et al. 1992. *J. Bacteriology* 174, 4594–4605). One such heat shock protein which is highly conserved in all living cells is approximately 70 kD in size and is referred to as hsp70. Hsp70 has been identified in *M. tuberculosis* (R. B. Lathigra, et al. 1988. *Nucleic Acids Res.* 16, 1636), *M. leprae* (K. K. McKenzie, et al. 1991. *J. Immunol.* 147, 312–319) and *M. paratuberculosis* (K. Stevenson, et al. 1991. *Nucleic Acids Res.* 19, 4552). Stevenson, et al. report a stretch of 133 amino acids (amino acids 407–540) in the *M. paratuberculosis* 70 kD heat shock protein which is 90% homologous to amino acids 131–264 of the *M. leprae* 70 kD heat shock protein and to amino acids 3–134 of the *M. tuberculosis* 71 kD heat shock protein. Certain terms used herein are defined as follows:

An "amplification primer" is a primer for amplification of a target sequence by primer extension or ligation of adjacent primers hybridized to the target sequence. For amplification by SDA, the amplification piers are preferably selected such that the GC content is low, preferably less than 70% of the total nucleotide composition of the probe. Similarly, for SDA the target sequence preferably has a low GC content to minimize secondary structure. The 3' end of an SDA amplification primer (the target binding sequence) hybridizes at the 3' end of the target sequence. The target binding sequence confers target specificity on the amplification primer. The SDA amplification primer further comprises a recognition site for a restriction endonuclease near its 5' end. The recognition site is for a restriction endonuclease which will nick one strand of a DNA duplex when the recognition site is hemimodified, as described by Walker, et al. (1992, *PNAS* 89, 392-396). For the majority of the SDA reaction, the amplification primer is responsible for exponential amplification of the target sequence. The SDA amplification primer may also be referred to as the "S" primer, e.g., $S_1$ and $S_2$ when a pair of amplification primers is used for amplification of a double stranded sequence. For other amplification methods which do not require attachment of specialized sequences to the ends of the target, the amplification primer generally consists essentially of only the target binding sequence. For example, amplification of a target sequence by PCR according to the invention will employ amplification primers consisting of the target binding sequences of the SDA primers described herein. These amplification primers are hybridized to the target sequence and extended by polymerase in the conventional PCR. The extension products are then displaced from the target sequence by heating, and a second cycle of primer hybridization and extension is initiated as is customary for PCR.

A "bumper primer" or "external primer" is a primer used in SDA which anneals to a target sequence upstream of the amplification primer such that extension of the bumper primer displaces the downstream amplification primer and its extension product. Bumper primers may also be referred to as "B" primers, e.g., $B_1$ and $B_2$ when a pair of bumper primers is used to displace the extension products of a pair of amplification primers. Extension of bumper primers is one method for displacing the extension products of amplification primers, but heating is also suitable.

The terms "target" or "target sequence" refer to nucleic acid sequences to be amplified by amplification primers. These include the original nucleic acid sequence to be amplified, the complementary second strand of the original nucleic acid sequence to be amplified, and either strand of a copy of the original sequence which is produced by the amplification reaction. These copies also serve as amplifiable target sequences by virtue of the fact that they also contain copies of the original target sequences to which the amplification primers hybridize.

Copies of the target sequence which are generated during the amplification reaction are referred to as "amplification products", "amplimers" or "amplicons".

The term "extension product" refers to the single-stranded copy of a target sequence produced by hybridization of an amplification primer and extension of the amplification primer by polymerase using the target sequence as a template.

The term "assay probe" refers to any of the oligonucleotides used in the detection or identification portion of an assay. In the present invention, the assay probes are probes used for complex-, group- or species-specific detection or identification of Mycobacteria. Detector probes, blocking oligonucleotides and capture probes are assay probes.

The "assay region" or "assay region sequence" is the portion of a target sequence, or other nucleic acid, to which an assay probe hybridizes. A specific assay region or assay region sequence is the assay region of the target sequence, or other nucleic acid, which it is desired to detect. A cross-hybridizing assay region or assay region sequence is the assay region of a target sequence, or other nucleic acid, which it is not desired to detect and to which an assay probe non-specifically cross-hybridizes. The cross-hybridizing assay region comprises a nucleotide sequence which varies by at least one nucleotide from the nucleotide sequence of the specific assay region.

As used herein, the term "species-specific" refers to detection or amplification in a species of organism without substantial detection or amplification in other species of the same genus or species of a different genus. "Genus-specific" refers to detection or amplification in the majority of the species of a genus, without substantial detection or amplification in the species of a different genus. "Group-" or "complex-specific" detection refers to detection or amplification in a selected group of related species (e.g., MAC) without substantial detection or amplification in other species of the same genus or species of a different genus.

SUMMARY OF THE INVENTION

The present invention provides methods for identification or detection of a species of organism or a group of related species by 1) species non-specific amplification of a target sequence followed by 2) species-, complex- or group-specific detection of the amplification products. Also provided is a target sequence which is amplifiable in multiple species of Mycobacteria using a single pair of amplification primers. The species from which the amplification products are derived is then identified by hybridization to specific assay probes which are capable of discriminating among the amplified targets of various species or groups of related organisms. Blocking oligonucleotides are employed to allow discrimination among species in which the assay regions of the amplified target sequences are sufficiently similar that they cross-hybridize with an assay probe. For amplification of a DNA K target sequence in Mycobacteria and detection of the amplification products of the MAC species, the blocking oligonucleotide reduces cross-hybridization sufficiently to allow as much as 100-fold discrimination among species which have as little as one variant nucleotide in the assay region.

DETAILED DESCRIPTION OF THE INVENTION

The inventive methods provide a means for amplifying analogous targets from multiple species using a single pair of amplification primers. Species-specificity is provided by the assay probes. The methods are capable of distinguishing or identifying species or related groups of species based on single nucleotide discrimination in the assay region by use of a blocking oligonucleotide. The blocking oligonucleotide may be applied to hybridization detection of any nucleotide sequence, whether previously amplified or not, to suppress cross-hybridization in situations where the assay regions of two species to be distinguished are not identical but are sufficiently similar that an assay probe cross-hybridizes to the assay region of the species not desired to be detected (i.e., the cross-hybridizing assay region) as well as the assay region of the species desired to be detected (i.e., the specific assay region).

Stevenson, et al., supra, reported a 133 amino acid sequence in the Mycobacterium paratuberculosis 70 kd heat shock protein which is 90% homologous among *M. paratuberculosis*, *M. tuberculosis* and *M. leprae*. This stretch of amino acids is encoded by nucleotides 1415–1814 of the DNA K gene sequence. GENBANK69 was searched with the nucleotides 1415–1814 sequence and it showed 87% homology to the corresponding *M. tuberculosis* nucleotide sequence. Significant homology with many other 70 kD heat shock proteins from a variety of prokaryotes and eukaryotes was also found. However, the *M. leprae* nucleotide sequence was not available in GENBANK69 for comparison. Using the alignment obtained for *M. paratuberculosis* and *M. tuberculosis*, two primers were selected for use in PCR amplification. The first primer was derived from the sense strand of the *M. paratuberculosis* sequence from nucleotides 1415–1434. The second primer was derived from the antisense strand of the *M. paratuberculosis* sequence from nucleotides 1763–1744. These primers were used in a PCR amplification reaction using several mycobacterial and non-mycobacterial DNAs as templates. PCR primers were synthesized on an Applied Biosystems 380B Synthesizer as recommended by the manufacturer, deprotected at 50° C. and purified through an Oligonucleotide Purification Cartridge (Applied Biosystems, Inc.).

PCR was performed in 25–100 µl reaction volumes consisting of 10 mM Tris-HCl pH 8.3, 50 mM KCl, 1.5 mM MgCl$_2$, 0.001% (w/v) gelatin, 200 µM dATP, 200 µM dCTP, 200 µM dGTP, 200 µM, TTP, 1.0 µM of each primer, 100 ng/100 µl of genomic DNA as template or 50 ng/100 µl plasmid DNA as template. The reactions were overlaid with mineral oil and heated to 95° C. for 5 min. 2.5 Units/100 µl of AMPLITAQ polymerase (Perkin Elmer Cetus, Norwalk, Conn.) were added and the cycling was started. The samples were typically incubated at 94° C. for 1 min. 30 sec., 37°–50° C. for 2 min., 72° C. for 3 min. for 25–30 cycles. This was followed by a 7 min. incubation at 72° C. and storage at 4° C.

There was a distinct 349 bp PCR product in all of the Mycobacteria tested, i.e., *M. africanum, M. avium, M. bovis, M. bovis-BCG, M. chelonae, M. fortuitum, M. gordonae, M. intracellulare, M. kansasii, M. scrofulaceum* and *M. tuberculosis*. The primers showed no cross-hybridization to *E. coli, N. asteroides* or *R. rhodochrous*. As smaller internal oligonucleotides based on this sequence are required for certain nucleic acid amplification methods, (e.g., SDA) it had to be determined whether there were highly conserved regions within this 349 bp product. The 349 bp amplification product (corresponding to nucleotides 1415–1763 of *M. paratuberculosis*) was subcloned and sequenced from the eleven Mycobacteria species (*M. africanum, M. avium, M. bovis, M. bovis-BCG, M. chelonae, M. fortuitum, M. gordonae, M. intracellulare, M. kansasii, M. scrofulaceum,* and *M. tuberculosis*). Sequencing was done using the Applied Biosystems 373A DNA sequencer using the Taq Dye Primer Cycle Sequencing Kit as recommended by the manufacturer.

Additional upstream (5') sequences of DNA K gene were obtained by analysis of sequence homologies between the 70K protein of *M. paratuberculosis* and *M. leprae*. Conserved regions were used to design degenerate PCR primers which amplified a 204 bp product from *M. avium, M. gordonae, M. kansasii* and *M. tuberculosis*. This product was subcloned into the EcoR1 site of pUC18 (Pharmacia). The clones were sequenced on an Applied Biosystems 373A sequencer using the Taq Dye Primer Cycle Sequencing Kit as recommended by the manufacturer. Upstream and downstream nucleotide sequences obtained in this manner were overlapped and aligned to generate complete sequences for each Mycobacteria species.

Amplification primers were designed based on analysis of sequence alignments of the DNA K gene for the various Mycobacteria species. These sequences are shown in SEQ ID NOS: 15–28, illustrating the nucleotide differences in the target sequence among the species. Ideally, primers were to be designed such that: 1) a single pair of amplification piers would amplify the target in multiple species of Mycobacteria, and 2) the resulting amplification products would include sequences between the primers (an assay region) with sequence variability which would allow species-, group- or complex-specific detection by hybridization of assay probes to the assay region. That is, the purpose was to develop an assay system in which the amplification was relatively species non-specific (i.e., the DNA K target would be amplified in most mycobacteria and possibly some closely related non-mycobacteria or, ideally, amplification would be genus-specific for Mycobacteria), but in which detection of the amplification products would be highly species-specific, group-specific or complex-specific. Such a system would be particularly useful for identifying, in a single amplification reaction, which species of a genus are present. Further, such a system would be useful where species-specific amplification primers cannot be designed for a particular target sequence. As discussed below, ideal non-cross-hybridizing, species-specific assay probes could not be designed for the assay region of the selected target sequence, illustrating the problem of designing non-specific amplification/specific detection systems for amplification methods which require a small target sequence, as smaller targets may exhibit minimal sequence variability among species. The use of the inventive blocking oligonucleotide to overcome this problem can be generally applied to any hybridization system to reduce non-specific cross-hybridization of an assay probe.

The amplification primers of the invention are useful in conventional nucleic acid amplification protocols such as PCR, SDA (lower-temperature or thermophilic) and 3SR. Specifically, any amplification protocol which utilizes cyclic, specific hybridization of primers to the target sequence, extension of the primers using the target sequence as a template and displacement of the extension products from the target sequence may employ the amplification primers of the invention. For amplification methods which do not require the specialized, non-target binding sequences of the amplification primers given in the attached SEQUENCE LISTING (e.g., PCR), the amplification primers may consist of the target binding sequences only. Amplification methods which require different specialized, non-target binding sequences than those given in the SEQUENCE LISTING (e.g., 3SR) may employ amplification primers comprising the target binding sequences of the amplification primers listed, with substitution of the sequence or structure required by the particular amplification method for the HincII site. Another restriction endonuclease recognition site appropriate for lower temperature SDA may also be substituted for the HincII site as is known in the art, or a restriction endonuclease recognition site appropriate for thermophilic SDA may be substituted when the target is amplified by thermophilic SDA.

Amplification primers were designed which amplified the region corresponding to nucleotides 1422–1475 of the *M. paratuberculosis* (*M. Ptb*) DNA K sequence (see FIG. 1). They were tested in an assay system for detection of the species of the MAC complex (*M. avium* and *M. intracellulare*, *M.a/i*). The predicted amplification product was generated in all of the MAC isolates described by Frothingham et. al. (1993. *J. Bacteriology* 175, 2818–2825), with detection of as few as 1–10 genomes of *M. avium* and *M. intracellulare*. In addition, the DNA K target sequence was amplified in all species of Mycobacteria tested except *M. xenopi* and *M. genavense* (see below). Further analysis suggested that the *M. genavense* isolate tested was actually an *M. xenopi* isolate. Cross-hybridization studies showed no target amplification in any of the non-mycobacterial organisms tested except *C. diphtheriae* and *R. rhodochrous*, which have a high degree of sequence similarity to *M. avium* and *M. intracellulare* in this region. However, the sequence of the assay region (the segment of the target sequence between the amplification primers to which the assay probes hybridize) in *C. diphtheriae* and *R. rhodochrous* is sufficiently different from the sequence of the *M. avium* and *M. intracellulare* assay region that the detector probes would not hybridize, thereby preventing detection of these organisms in the assay.

The Mycobacteria species from which the amplification products are generated, or from which unamplified nucleic acids are derived, are identified or distinguished by hybridization to assay probes which confer species-, group- or complex-specificity on the detection portion of the assay. For detection by hybridization, the detector probes are typically tagged with a detectable label. The detectable label is a moiety which can be detected either directly or indirectly as an indication of hybridization of the probe to the target nucleic acid. For direct detection of the label, probes may be tagged with a radioisotope and detected by autoradiography or tagged with a fluorescent moiety and detected by fluorescence as is known in the art. Alternatively, the probes may be indirectly detected by tagging with a label which requires additional reagents to render it detectable. Indirectly detectable labels include, for example, chemiluminescent agents, enzymes which produce visible reaction products and ligands (e.g., haptens, antibodies or antigens) which may be detected by binding to labeled specific binding partners (e.g., antibodies or antigens/haptens). Particularly useful labels include biotin (detectable by binding to labeled avidin or streptavidin) and enzymes such as horseradish peroxidase or alkaline phosphatase (detectable by addition of enzyme substrates to produce colored reaction products). Biotin and other ligands are also useful for tagging capture probes to allow mobilization of the capture probe and the complex to which it is hybridized on a solid phase by binding to the appropriate specific binding partner. Methods for adding such labels to, or including such labels in, oligonucleotides are well known in the art and any of these methods are suitable for use in the present invention.

One method for detecting the amplification products is by polymerase extension of a primer specifically hybridized to the target sequence. The primer is labeled as described above, e.g., with a radioisotope, so that the label of the primer is incorporated with the primer into the amplification product. This method is described in more detail by Walker, et al. (1992) *Nucl. Acid Res.* and *PNAS*, supra. A second method for detecting amplified target and control sequences is a chemiluminescent assay method in which amplified products are detected using a biotinylated oligonucleotide capture probe and an enzyme-conjugated oligonucleotide detector probe as as described by Spargo, et al. (1993. *Molec. Cell. Probes* 7, 395–404). After hybridization of these two probes to different sites on an amplified target sequence, the complex is captured on a streptavidin-coated microwell plate, and the chemiluminescent signal is developed and read in a luminometer. This detection method can be performed in less than two hours and is sensitive enough to detect as few as one pre-amplification target sequence.

Figure 1:
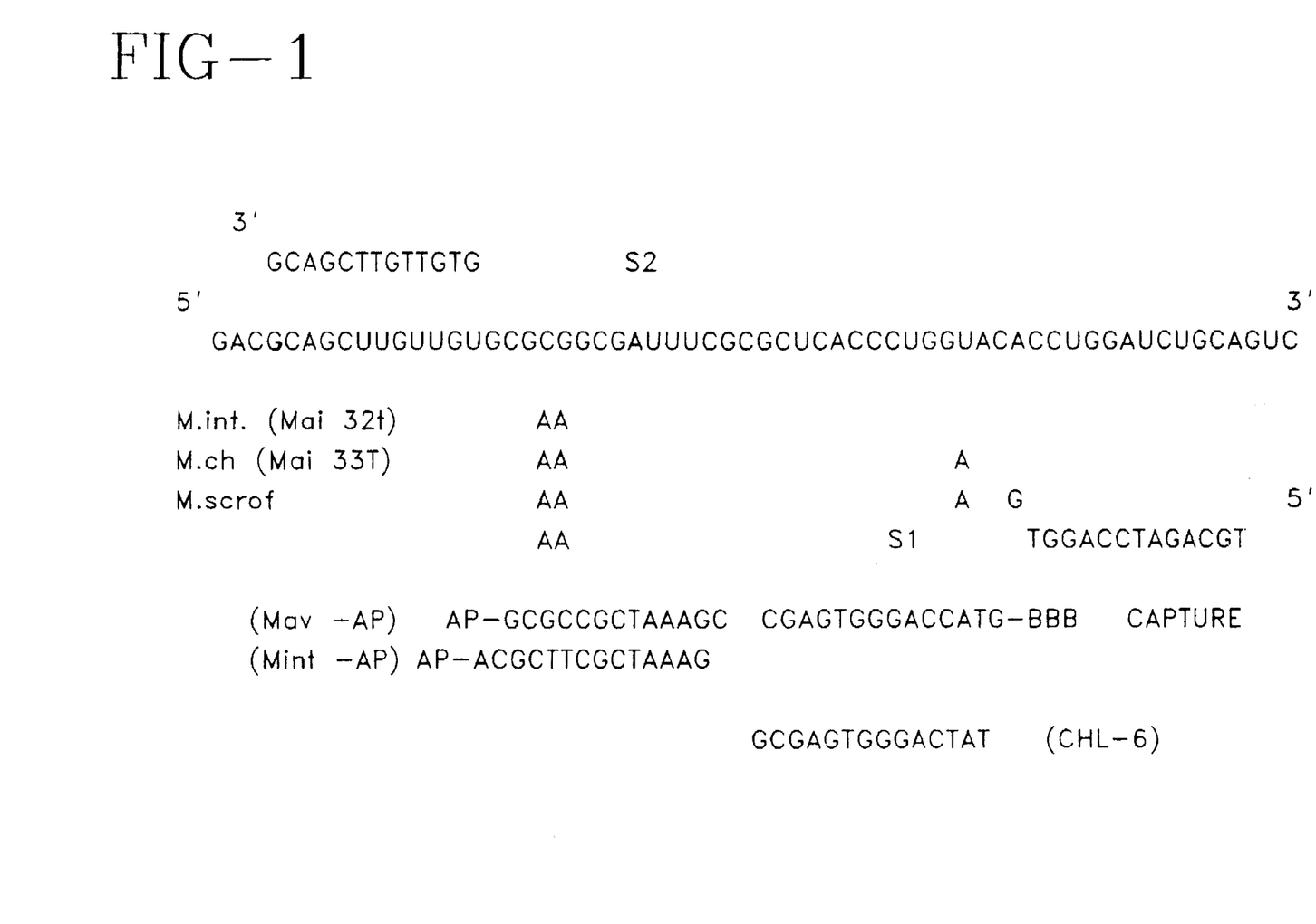
FIG. 1 illustrates the DNA K target sequence in *M. avium* (top sequence), *M. intracellulare* (*M. int.*), *M. chelonae* (*M. ch*) and *M. scrofulaceum* (*M. scrof*). The sequences and hybridization sites of the amplification primers, capture and detector probes and blocking oligonucleotide exemplified in Example 4 are also shown.

The DNA K amplification products generated by the amplification primers comprise unique assay region sequences which allow identification of the Tb complex organisms, MAC organisms, *M. kansasii* strains and others by hybridization of the assay region to assay probes which confer species-specificity or complex-specificity. Analysis of sequence alignments showed that discrimination of single nucleotide variations in the assay region would be necessary to specifically detect MAC organisms. Such discrimination was not possible using hybridization of the detector probe alone. The first assay experiments indicated cross-hybridization between MAC species and *M. chelonae*. The difference between the *M. chelonae* and *M. intracellulare* assay regions (i.e., between the cross-hybridizing assay region and the specific assay region) was one nucleotide in the capture probe. See FIG. 1. This cross-hybridization in the detection portion of the assay was significantly reduced by the addition of a blocking oligonucleotide, which improved the specificity of the assay so that as little as a single nucleotide sequence difference could be discriminated. Although the mechanism by which the blocking oligonucleotide improves assay specificity has not been rigorously demonstrated, it may be that the blocking oligonucleotide hybridizes preferentially to the cross-hybridizing *M. chelonae* assay region and prevents non-specific hybridization of the biotinylated *M. a/i* capture probe to this sequence. As shown in FIG. 1, the blocking oligonucleotide is not biotinylated and has a sequence that is the exact Watson-Crick complement of the cross-hybridizing *M. chelonae* assay region at the site where the non-specific hybridization of the capture probe occurs. A DNA duplex formed by the hybridization of two perfectly complementary strands is at least several kcal/mol more stable than the corresponding duplex containing a single mismatch. The blocking oligonucleotide may therefore hybridize preferentially to the cross-hybridizing *M. chelonae* assay region and less efficiently, or not at all, to the specific assay region of *M. intracellulare*. The presence of the blocking oligonucleotide does not appear to interfere with hybridization of the capture probe to the specific assay region of *M. intracellulare*. The blocking oligonucleotide thus renders the *M. chelonae* target undetectable by preventing its hybridization to the capture probe and subsequent immobilization through streptavidin. At the same time, however, the blocking oligonucleotide does not appreciably diminish the sensitivity of *M. intracellulare* detection. When using the blocking oligonucleotide in the assay, a 100-fold discrimination of the single nucleotide change was achieved.

As illustrated by Examples 2 and 3, blocking oligonucleotides may be applied to nucleic acid hybridization assays of all kinds to reduce cross-hybridization (i.e., non-specific hybridization) of an assay probe to assay regions of targets which it is not desired to detect. For example, the specificity of hybridization in solid phase assays such as dot blots and Southern blots, or solution hybridizations may be improved by employing blocking oligonucleotides according to the invention which hybridize preferentially to the cross-hybridizing assay region—with or without prior amplification of the target sequence. Whether or not a blocking oligonucleotide will be necessary depends on a complex interaction of the nature and extent of the sequence differences between the cross-hybridizing assay region and the specific assay region. However, if cross-hybridization is detected in any particular hybridization assay, the appropriate blocking oligonucleotide can be designed as described herein, without the use of further inventive skill, based on the sequence of the cross-hybridizing assay region to be eliminated from detection.

As shown in FIG. 1, the target binding sequences of the amplification primers exemplified herein hybridize to conserved regions of the DNA K gene, thereby providing amplification of the target sequence in multiple species of Mycobacteria (i.e., species non-specific amplification). The assay region flanked by the amplification primers contains sequence variations among the species. The variations may be as little as a single nucleotide difference between species to be distinguished. Given the DNA K sequence alignments for the mycobacteria obtained from SEQ ID NOS: 15–28 and the present disclosure of the sequence requirements of the target region (two highly conserved regions flanking a variable region of a suitable size for amplification), additional target sequences for species non-specific amplification and species -or group-specific detection can be identified in the DNA K gene. For example, species non-specific amplification primers may be designed which hybridize to the conserved regions at nucleotides 1665–1684 and 1745–1763. In the assay region flanked by these amplification primers, M. kansasii differs from species of the M. tuberculosis complex by a single nucleotide at position 1708. A blocking oligonucleotide which is the exact complement of the tuberculosis sequence in this region can be used to reduce or eliminate non-specific cross-hybridization of an assay probe to M. tuberculosis complex targets when M. kansasii is to be detected. Similarly, the single nucleotide difference between M. africanum and the species of the M. tuberculosis complex at nucleotide 1720 can be used for design of a blocking oligonucleotide to reduce cross-hybridization of assay probes directed to this region. M. intracellulare and M. scrofulaceum can be distinguished on the basis of the single nucleotide difference at position 1701 using the appropriate blocking oligonucleotide. Further, these criteria can easily be applied to other targets (in Myocbacteria or other species) for which the nucleotide sequence is known, to design analogous non-specific amplification/specific detection assay systems.

The following experimental examples are provided to illustrate certain embodiments of the invention but are not to be construed as limiting the invention as defined by the appended claims. The oligonucleotides referred to in the examples are described below. The target binding sequences of the amplification primers ($S_1$ and $S_2$) are underlined. The synthetic target sequences have a 3' poly A tail in order to reduce the possibility that these sequences could be used as templates for amplification.

| SEQ ID NO:1 | SDA $S_1$ Primer ($S_1$ in FIG. 1), 37mer: |
| --- | --- |
| | Binds to M. Ptb nucleotides 1422–1434. |
| | 5'TTGAATAGTCTCTTACAAGTTGACTGCAGATCCAGGT 3' |
| SEQ ID NO:2 | SDA $S_2$ Primer ($S_2$ in FIG. 1), 37mer: |
| | Binds to M. Ptb nucleotides 1475–1463. |
| | 5'TTGTTGTAAGAGACTATTGTTGACGCAGCTTGTTGTG 3' |
| SEQ ID NO:3 | SDA $B_1$ Bumper, 13mer: |
| | Bind to M. Ptb nucleotides 1400–1412. |
| | 5'GCCGACGACAACC 3' |
| SEQ ID NO:4 | SDA $B_2$ Bumper, 13mer: |
| | Bind to M. Ptb nucleotides 1496 –1484. |
| | 5'CGGTCAGCTCGAA 3' |
| SEQ ID NO:5 | SDA $D_1$ Detector, 15mer: |
| | Binds to M. Ptb nucleotides 1435–1449. |
| | 5'GTACCAGGGTGAGCG 3' |
| SEQ ID NO:6 | Assay Capture Probe ("Capture"), 14mer: |
| | Binds to M. Ptb nucleotides 1435–1448. |
| | 5'BBB-GTACCAGGGTGAGC 3' (BBB = 3 biotin groups) |
| SEQ ID NO:7 | M. avium Detector Probe ("Mav AP"), 13mer: |
| | Binds to M. Ptb nucleotides 1450–1462. |
| | 5'CGAAATCGCCGCG-AP 3' (AP = alkaline phosphatase) |
| SEQ ID NO:8 | M. intracellular Detector Probe ("Mint AP"), 14mer: |
| | Binds to M. Ptb nucleotides 1451–1464. |
| | 5'GAAATCGCTTCGCA-AP 3'(AP = alkaline phosphatase) |
| SEQ ID NO:9 | Blocking Probe ("CHL-1"), 14mer: |
| | Binds to M. Ptb nucleotides 1435–1449. |
| | 5'GTATCAGGGTGAGC 3' |
| SEQ ID NO:10 | Blocking Probe ("CHL-4"), 15mer: |
| | Binds to M. Ptb nucleotides 1435–1449. |
| | 5'GTATCAGGGTGAGCG3' |
| SEQ ID NO:11 | Blocking Probe ("CHL-6"), 14mer: |
| | Binds to M. Ptb nucleotides 1436–1449. |
| | 5'TATCAGGGTGAGCG 3' |
| SEQ ID NO:12 | M. avium Synthetic Target Sequence: |
| 5'GACGCAGCUU | GUUGUGCGCG GCGAUUUCGC GCUCACCCUG GUACACCUGG AUCUGCAGUC AAAAA 3' |
| SEQ ID NO:13 | M. intracellular Synthetic Target Sequence: |
| 5'GACGCAGCUU | GUUGUGCGAA GCGAUUUCGC GCUCACCCUG GUACACCUGG AUCUGCAGUC AAAAA 3' |
| SEQ ID NO:14 | M. chelonae Synthetic Target Sequence: |
| 5'GACGCAGCUU | GUUGUGCGAA GCGAUUUCGC GCUCACCCUG AUACACCUGG AUCUGCAGUC AAAAA 3' |

The above amplification primers include the specialized sequences required for SDA. The target binding sequences of the amplification piers are shown in FIG. 1 with their hybridization sites on the DNA K gene sequence. The sequences of the capture and detector probes and blocking oligonucleotide used in Example 4 are also shown in FIG. 1, with their hybridization sites.

EXAMPLE 1

SDA Methods

SDA was performed generally as described by Walker, et. al., *Nucl. Acids Res.*, supra, substituting dUTP for TTP to allow removal of contaminating amplicons. The final concentration of components was 45 mM KiPO$_4$ pH 7.6, 6 mM magnesium acetate (MgAc), 0.1 mg/ml BSA, 15% (v/v) dimethylsulfoxide, 3% (v/v) glycerol (supplied by the stock solutions of exo- klenow and HincII), 50 ng human placental DNA, 0.5 mM dUTP, 0.2 mM dGTP, 0.2 mM dCTP, 0.2 mM dAsTP (2'-deoxyadenosine 5'-O-(1-thiotriphosphate)), 0.5 µM primers (SEQ ID NO: 1 (S$_1$) and SEQ ID NO: 2 (S$_2$)), 0.05 µM bumpers (SEQ ID NO: 3 (B$_1$) and SEQ ID NO: 4 (B$_2$)), 4 units exo- klenow, 150 units HincII, 1 unit UDG, 1 unit UDGi (uracil DNA glycosylase inhibitor) and mycobacterial genomic DNA. The amplification reaction was incubated at 40° C. for 2 hours.

All reagents except exo- klenow, HincII, UDG, UDGi, and MgAc were mixed in a volume of 42 µl. This solution was heated at 95° C. for 3 minutes to denature the genomic DNA and then incubated at 40° C. for 3 minutes to allow the amplification and bumper primers to anneal. One microliter containing one unit UDG was added, mixed and allowed to incubate for 30 minutes at 40° C. in order to decontaminate the sample. Seven microliters containing exo-klenow, HincII, UDGi, and MgAc were added and mixed, resulting in a final volume of 50 µl. The samples were incubated at 40° C. for 2 hours, then heated to 95° C. for 3 minutes to stop the reaction.

General (i.e., not species or complex-specific) detection of amplification products was by primer extension as described by Walker, et. al., *Nucl. Acids Res.*, supra, also substituting dUTP. A 5 µl aliquot of each sample was mixed with 5 µl of a solution containing 50 mM KiPO$_4$, 6 mM MgCl$_2$, 0.5 mM dUTP, 0.2 mM dGTP, 0.2 mM dCTP, 0.2mM dAsTP, 0.2 µM 5'-$^{32}$P detector probe (SEQ ID NO: 5 (D$_1$)). The 10 µl samples were then heated to 95° C. for 3 minutes to denature the DNA, cooled at 37° C. for 3 minutes to anneal the detector probe to the target. One microliter (4 units/µl) exo- klenow was then added. The samples were incubated for 10 minutes at 37° C. followed by the addition of Stop Solution (95% of formamide, 20 mM EDTA, 0.05% Bromophenol Blue, 0.05% Xylene Cyanol—USB). Samples were then heated to 95° C. for 3 minutes and analyzed by denaturing gel electrophoresis on 8% polyacrylamide gels followed by autoradiography.

Although the following examples illustrate amplification by conventional, lower temperature SDA, thermophilic SDA (SDA conducted at increased reaction temperature using heat-tolerant enzymes) is also a suitable SDA system. dUTP may be substituted for TTP in thermophilic SDA as in conventional SDA to allow removal of contaminating amplicons as in lower-temperature SDA. For example, thermophilic SDA may be performed as follows: 25 mM KiPO$_4$ pH 7.6, 6.7 mM MgCl$_2$, 0.1 mg/ml BSA, 5% (v/v) dimethylsulfoxide, 5% (v/v) glycerol, 50 or 500 ng human placental DNA, 1.4 mM dCsTP (thio-substituted dCTP), 0.5 mM dGTP, 0.5 mM dATP, 0.5 mM dUTP, 0.5 µM amplification primers, 0.05 µM bumper primers, 60 units Bst polymerase, 20 units BsoB1 restriction endonuclease, and mycobacterial genomic DNA. Other suitable heat-stable polymerases and restriction endonucleases may be substituted as is known in the art.

Thermophilic SDA reactions are prepared in a manner similar to lower-temperature SDA reactions. In the above example, all reagents except Bst, BsoB 1, glycerol and MgCl$_2$ were mixed in a volume of 42 µl. This solution was heated at 95° C. for 3 minutes to denature the genomic DNA and then at 55° C. for 5 minutes to allow the amplification and bumper primers to anneal. Eight microliters containing Bst, BsoB1, MgCl$_2$ and glycerol were added and mixed. The final volume was 50 µl and this was incubated at 55° C. for 30 minutes. The amplification reaction was stopped by heating to 95° C. for 3 minutes.

The amplification products of thermophilic SDA were detected by extension of the detector primer as described above. Ten genomes of *M. avium* could be detected in thermophilic SDA reactions, giving a sensitivity of between 1 and 10 genomes. In the presence of 50 ng human DNA the reaction appeared to be complete within 30 minutes. In the presence of 500 ng human DNA the reaction was completed within 20 minutes. Amplification factors in both reactions were about $10^9$, whereas lower-temperature SDA (as in Example 1) generally resulted in amplification factors of about $10^7$. If dUTP is not substituted for TTP in thermophilic SDA, higher amplification factors may be obtained, on the order of about $10^{10}$.

Chemiluminescent Assay Methods

Capture probes labeled at the 5' terminus with three biotin residues and detector probes labeled at the 3' terminus with alkaline phosphatase (AP) were prepared as described by Spargo, et al. (1993. *Molec. Cell. Probes* 7, 395–404).

Microwell plates coated with biotinylated bovine serum albumin (biotin*BSA) (Pierce, Rockford, Ill.) were prepared essentially as described by Spargo, et al., supra, with minor modifications. Biotin*BSA was diluted to 5 µl/ml in 0.05M NaCarbonate pH 9.6 (BRL, Bethesda, Md.), pipetted into each well (200 µL/well, 1 µg/well) of microwell plates (Labsystems, Labproducts™, Research Triangle Park, N.C.), and incubated at room temperature overnight. The wells were washed twice (375 µL/wash) using FTA hemagglutination buffer (Becton Dickinson Microbiology Systems, Cockeysville, Md.) pH 7.2. The wash buffer was discarded by inversion. Streptavidin (Scripps, 10 µg/ml) in hemagglutination buffer was added to the biotin*BSA coated microtiter wells (100 µL/well, 1 µg/well). Plates were covered and incubated overnight at room temperature. Unbound streptavidin was discarded by inversion and blocking buffer (300 µL/well) (hemagglutination buffer pH 7.2, 0.05% w/v bovine serum albumin—Sigma Chemical Co., St. Louis, Mo.) was added. The plates were covered, incubated overnight at room temperature, and the blocking buffer was discarded by inversion. Wells were washed twice with hemagglutination buffer (375 µL/well), then once using hemagglutination buffer with 2% w/v trehalose (375 µL/well) (Fluka, Konkonkoma, N.Y.). The FTA/Trehalose buffer was discarded by inversion. Plates were dried for 1 hour at 37° C. and then sealed in mylar pouches with silica desiccant (Microcaps™, Multiform Dessicants), and stored overnight at room temperature prior to use. The plates were stored thereafter at 2°–8° C. The chemiluminescent assay was performed essentially as described by Spargo, et al., supra.

Oligonucleotide Synthesis

Single stranded synthetic target DNAs (SEQ ID NO: 12, SEQ ID NO: 13, SEQ ID NO: 14), containing dU in place of dT, were synthesized as exact complements of target strands generated by amplification. These were diluted into 45 mM KPO$_4$ pH 7.6, 3% glycerol, 0.1 mg/ml bovine serum albumin, 15% DMSO, 5 µM each SEQ ID NO: 1 and SEQ ID NO: 2, 0.5 µM each SEQ ID NO: 3 and SEQ ID NO: 4.

Amplification and bumper primers for SDA were synthesized using an ABI 380B synthesizer using B cyanoethyl phosphoramidite chemistry as recommended by the manufacturer. The oligonucleotides were deprotected at 55° C. and gel purified as previously described (F. M. Ausubel, et. al. 1987. *Current Protocols in Molecular Biology*, Greene Publishing Associates and Wiley-Interscience, N.Y.). Blocking oligonucleotides were synthesized as described for the SDA primers. The concentrations of capture and detector nucleotides were optimized for reagent lot to reduce backgrounds and maximize the difference between signal and background.

EXAMPLE 2

Synthetic targets were used in the chemiluminescent assay system for detection of the MAC complex mycobacteria to evaluate the effect of blocking oligonucleotides on cross-hybridization in the detection portion of the assay. *M. chelonae* was used as the cross-hybridizing control.

Synthetic targets (SEQ ID NO: 12, SEQ ID NO: 13, SEQ ID NO: 14) were diluted and heated at 95° C. for 3 minutes to denature the DNA. The solutions were cooled for 5 minutes at room temperature and 10 µL of the denatured sample was added to each well of a prepared microwell plate. Immediately thereafter, 90 µL/well of hybridization mix (0.051M Trizma base (Sigma), 0.9M or 0.25M NaCl (Fisher), 0.05 mM ZnCl$_2$ (Sigma), 0.1% bovine serum albumin (Sigma), 0.2% NaN$_3$, 10.2 µg/ml salmon sperm DNA (Sigma), 2% Trehalose (Quadrant), pH 7.0, capture probe SEQ ID NO: 6 10 nM, detector probes SEQ D NO: 7 at 5 nM and SEQ ID NO: 8 at 10 nM, blocking probe SEQ ID NO: 9 at 10 nM (if required) was added. The microwell plate was covered and incubated for 45 minutes at 37° C. Three stringency washes (10 mM Trizma base (Sigma) 0.1% w/v bovine serum albumin (Sigma), 0.01% Nonidet P-40 (Sigma), 250 mM NaCl, 0.1% NaN$_3$ pH 7.5), 100 µL/well, were performed at room temperature. Lumiphos™ 530 (100 µL/well, Lumigen Inc., Detroit, Mich.) substrate was added, the plates were covered and incubated for 30 minutes at 37° C. Luminescence (RLU) was read on a microwell plate luminometer (Labproducts™, Research Triangle Park, N.C.) at 37° C., using a 2 second/well integration time.

The results of evaluation of the *M. chelonae* blocking oligonucleotide are shown in Table 1. These results demonstrate the ability of the blocking oligonucleotide to suppress the cross-hybridization of the capture probe with the assay region of the *M. chelonae* synthetic target sequence. SEQ ID NO: 7 is the specific detector probe for *M. avium*. This detector probe in combination with the capture probe does not cause significant cross-hybridization with the assay region of the *M. chelonae* target sequence. However, addition of the blocking oligonucleotide completely eliminates the minor cross-hybridization seen without affecting the specific signal. SEQ ID NO: 8 is the *M. intracellulare* specific detector probe. This detector probe in combination with the capture probe cross-hybridizes significantly with the assay region of the *M. chelonae* target sequence. Addition of the blocking oligonucleotide (SEQ ID NO: 9) decreased cross-hybridization 4-fold without decreasing sensitivity, and provided 10-fold discrimination between signal from the specific target (*M. intracellulare*) and signal from the non-specific target (*M. chelonae*).

TABLE 1

Evaluation of *M. chelonae* CHL-1 Blocker Oligo
Relative Light Units (RLU)

| Detector | Syn. Target | Attomoles Syn. Target | No Blocking Oligo | | W/Blocking Oligo | |
|---|---|---|---|---|---|---|
| | | | 0.9M NaCl | 0.25M NaCl | 0.9M NaCl | 0.25M NaCl |
| *M. avium* | *M. avium* | 0 | 8 | 9 | 5 | 10 |
| | | 4000 | 3693 | 2237 | 3744 | 2018 |
| | | 32000 | >20000 | >20000 | >20000 | 13566 |
| *M. intracell.* | *M. intracell.* | 0 | 8 | 9 | 4 | 7 |
| | | 4000 | 2582 | 1603 | 2523 | 1438 |
| | | 32000 | >20000 | 10940 | 13244 | 9974 |
| *M. avium* | *M. chelonae* | 0 | 7 | 7 | 4 | 4 |
| | | 4000 | 11 | 6 | 8 | 5 |
| | | 32000 | 87 | 18 | 35 | 14 |
| *M. intracell.* | *M. chelonae* | 0 | 6 | 5 | 4 | 4 |
| | | 4000 | 954 | 404 | 218 | 105 |
| | | 32000 | 2989 | 2678 | 2028 | 785 |

EXAMPLE 3

Cross-hybridization in the detection portion of the assay was evaluated as in Example 2, testing SEQ ID NO: 10 as the *M. chelonae* blocking oligonucleotide in place of SEQ ID NO: 9. The results are shown in Table 2. Using the synthetic targets, the addition of the blocking oligonucleotide decreased the specific signal by 30% but also decreased cross-hybridization up to 40-fold with 100-fold discrimination between signal from the specific target (*M. intracellulare* and *M. avium*) and signal from the non-specific target (*M. chelonae* target) at 45° C. In this experiment, blocking oligonucleotide SEQ ID NO: 10 was more successful than SEQ ID NO: 9 in suppressing cross-hybridization but also reduced specific signal.

TABLE 2

Evaluation of M. chelonae CHL-4 BLocker Oligo
Relative Light Units (RLU)

| Detector | Syn. Target | Attomoles Syn. Target | No Blocking Oligo | | W/Blocking Oligo | |
|---|---|---|---|---|---|---|
| | | | 37° C. Hyb | 45° C. Hyb | 37° C. Hyb | 45° C. Hyb |
| M. avium | M. avium | 0 | 12 | 11 | 10 | 9 |
| | | 4000 | 2578 | 1315 | 1718 | 816 |
| | | 32000 | 18261 | 10957 | 11661 | 6041 |
| M. intracell. | M. intracell. | 0 | 8 | 9 | 4 | 7 |
| | | 4000 | 1766 | 661 | 1139 | 495 |
| | | 32000 | 9551 | 6658 | 8747 | 4377 |
| M. avium | M. chelonae | 0 | 14 | 11 | 11 | 7 |
| | | 4000 | 26 | 12 | 11 | 7 |
| | | 32000 | 42 | 19 | 11 | 7 |
| M. intracell. | M. chelonae | 0 | 11 | 11 | 11 | 8 |
| | | 4000 | 1020 | 83 | 21 | 12 |
| | | 32000 | 3599 | 1945 | 141 | 54 |

EXAMPLE 4

The effect of hybridization temperature on cross-hybridization in the detection portion of the assay was evaluated as in Example 2, testing SEQ ID NO: 11 as the M. chelonae blocking oligonucleotide in place of SEQ ID NO: 9. The capture probe and blocking oligonucleotide were present at a concentration of 5 nM each. Capture probe, detector probes, synthetic target and the blocking oligonucleotide were incubated in the prepared microwell plate for 45 min. at 30° C., 37° C., 42.5° C., 45° C., or 50° C. The results are shown in Table 3. In general, higher hybridization temperatures resulted in reduced signal from M. avium and M. intracellulare, and increased signal from M. chelonae. Lower hybridization temperatures resulted in equivalent or higher signal from M. avium and M. intracellulare, but also increased signal from M. chelonae. Temperature optimization for assay hybridization using the blocker probe SEQ ID NO: 11 indicated that 42.5° C. hybridization gave the best ratio of specific- to non-specific signal and provided >100 fold discrimination between signals from the specific and non-specific targets. Such hybridization temperature studies are routine for optimizing hybridization of a probe or primer to its target sequence and would usually be performed to optimize the performance of any blocking oligonucleotide.

TABLE 3

MAI Blocking Assay: CHL-6 Blocking Oligo
Hybridization of Capture Probe, M. avium detector probe,
M. intracellulare detector probe, CHL-6 Blocking oligo with synthetic target

| Syn. Target | Attomoles Syn. Target | Molecules of Target | Relative Light Units |
|---|---|---|---|
| M. avium | 0 | 0 | 19 |
| | 250 | $1.5 \times 10^8$ | 84 |
| | 500 | $3 \times 10^8$ | 185 |
| | 32000 | $2 \times 10^{10}$ | 9117 |
| M. intracellulare | 0 | 0 | 9 |
| | 250 | $1.5 \times 10^8$ | 95 |
| | 500 | $3 \times 10^8$ | 205 |
| | 32000 | $2 \times 10^{10}$ | 8273 |
| M. chelonae | 0 | 0 | 11 |
| | 250 | $1.5 \times 10^8$ | 11 |
| | 500 | $3 \times 10^8$ | 14 |
| | 32000 | $2 \times 10^{10}$ | 73 |

EXAMPLE 5

Cross-hybridization was evaluated in amplification reactions containing $10^5$ genomes from each of a variety of mycobacterial species, $10^6$ genomes of each of a variety of non-mycobacterial species or the synthetic targets (controls). Each SDA reaction was run in duplicate as described above and each synthetic target control was also run in duplicate. Completed SDA reactions and/or synthetic target dilutions were heated at 95° C. for 3 minutes to denature the DNA. The solutions were cooled for 5 minutes at room temperature and 10 µL of the denatured sample was added to each well of a prepared microwell plate. Immediately thereafter, 90 µL/well of hybridization mix (0.051M Trizma base (Sigma), 0.25M NaCl (Fisher), 0.05 mM ZnCl$_2$ (Sigma), 0.1% bovine serum albumin (Sigma), 0.2% NaN$_3$, 10.2 µg/ml salmon sperm DNA (Sigma), 2% Trehalose (Quadrant), pH 7.0, capture probe SEQ ID NO: 6 at 5 mM, detector probes SEQ ID NO: 7 at 5 nM and SEQ ID NO: 8 at 10 nM, blocking oligonucleotide SEQ ID NO: 11 at 5 nM were added. The microwell plate was covered and incubated for 45 minutes at 42.5° C. Three stringency washes (10 mM Trizma base (Sigma) 0.1% w/v bovine serum albumin (Sigma), 0.01% Nonidet P-40 (Sigma), 250 mM NaCl, 0.1% NaN$_3$ pH 7.5), 100 µL/well, were performed at room temperature. Lumiphos™ 530 (100 µL/well, Lumigen Inc., Detroit, Mich.) substrate was added, the plates were covered and incubated for 30 minutes at 37° C. Luminescence (RLU) was read on a microwell plate luminometer (Labproducts™, Research Triangle Park, N.C.) at 37° C., using a 2 second/well integration time.

The Mycobacteria species tested were M. intracellulare, M. tuberculosis, M. bovis, M. bovis BCG, M. kansasii, M. fortuitum, M. paratuberculosis, M. gordonae, M. chelonae, M. microti, M. africanum, M. flavescens, M. genavense, M. gastri, M. haemophilum, M. avium, M. avium Complex, M. marinum, M. scrofulaceum, M. szulgai, M. terrae, M. xenopi, M. dienhoferi, M. lufu, M. nonchromogenicum, M. phei, M. simiea, M. smegmatis, and M. thermoresistible. Extension of the hybridized $^{32}$P-labeled primer showed that the expected amplification product was generated in all mycobacterial species tested except for M. xenopi and M. genavense. Amplification in M. gordonae was suppressed because of the two nucleotide mismatch at the 3' end of the S$_2$ primer. Amplification should occur at normal levels if the hybridization site of the amplification primer is moved slightly to eliminate the mismatch. Further analysis suggested that the M. genavense DNA used in this experiment was actually M. xenopi. The closely related non-mycobacterial species tested were C. diphtheriae, P. acnes, N. asteroides, N. brasiliensis, A. israelii, Streptomyces, R.

rhodochrous, Adenovirus, *A. lwoffi, B. pertussis, C. albicans, C. ulcerans, E. aerogenes, E. cloacae, E. coli, F. meningisepticum, H. influenza, K. pneumoniae, L. monocytogenes, M. osloensis, M. morganii, N. otitidiscaviarum, N. gonorrhoeae, N. lactamica, N. meningitidis, O. turlata, P. aeruginosa, P. vulgaris, S. epidermidis, S. faecalis, S. marcescens, S. boydii, S. dysenteriae, S. flexneri, S. sonnei, S. aureus, S. faecalis, S. pneumoniae* and *S. pyogenes*. Amplification of 10⁶ copies/rxn of genomic DNA from these closely related organisms produced amplification products only in *C. diphtheriae, R. rhodochrous* and *S. pneumoniae*. However, analysis of the available sequence information for these species revealed that although the hybridization sites of the amplification primers are sufficiently similar to the Mycobacteria for amplification to occur, the sequences of the sites of hybridization of the detector probe are sufficiently different that the detection portion of the assay would prevent detection of amplified target sequences from *C. diphtheriae* and *R. rhodochrous*. When *S. pneumoniae* was amplified again using a previously unopened vial of DNA, there were no amplification products generated, indicating that the initial positive result was due to contamination.

The results of species- and complex-specific detection of the amplification products are shown in Table 4. With the blocking oligonucleotide present, only *M. avium, M. intracellulare* and *M. avium* Complex are strongly positive. *M. paratuberculosis* (thought to be a subspecies of *M. avium*), *M. scrofulaceum, M. lufu* and *M. haemophilum* were also detected but with significantly reduced signal as compared to the MAC species. Additional studies showed that the *M. scrofulaceum* DNA sample tested was contaminated with non-*M. scrofulaceum* DNA which was detectable in the assay. *M. lufu* has not been isolated in the past several years and, as it is not considered a human pathogen, it is unlikely to occur in a sample being tested for MAC organisms. None of the other Mycobacteria or non-mycobacterial organisms tested showed any cross-hybridization in the detection portion of the assay.

TABLE 4

CROSS-HYDRBIDIZATION STUDIES - MAI ASSAY RESULTS
Organisms at 10⁵ for SDA rxns

| ORGANISM | AVG RLU | ORGANISM | AVG RLU |
|---|---|---|---|
| 0 | 7 | M. terrae | 25 |
| M. tuberculosis | 7 | M. xenopi | 11 |
| M. bovis | 8 | M. dienhoferi | 64 |
| M. bovis/bcg | 11 | M. lufu | 2592 |
| M. avium | 6633 | M. nonchromogenicum | 12 |
| M. intracellulare | 6824 | M. phei | 53 |
| M. kansasii | 15 | M. simiea | 41 |
| M. paratuberculosis | 739 | M. smegmatis | 10 |
| M. fortuitum | 39 | M. thermoresistible | 64 |
| M. gordanae | 10 | | |
| M. chelonea | 44 | NON-MYCOS | |
| M. microti | 22 | | |
| M. genavense | 7 | Actinomyce israelii | 7 |
| M. africanum | 7 | Corynebacterium diptheriae | 9 |
| M. chelonea (abcess) | 35 | Nocardia asteroides | 13 |
| M. flavescens | 9 | Norcardia brasiliensis | 8 |
| M. gastri | 41 | Propionibacterium acnes | 9 |
| M. haemophilum | 207 | Streptomyces griseus | 12 |
| M. avium complex | 3013 | Rhodococcus rhodochrous | 9 |
| M. marinum | 40 | | |
| M. scrofulaceum | 1530 | | |
| M. szulgai | 25 | | |

| Synthetic Controls attomoles/test | M.avium avg. RLU | M. intracellulare avg. RLU | M.chelonae avg. RLU |
|---|---|---|---|
| 0 | 9 | 10 | 9 |
| 250 | 80 | 64 | 11 |
| 500 | 123 | 117 | 11 |
| 32000 | 5131 | 7784 | 83 |

What is claimed is:

1. A set of oligonucleotides for amplification of a DNA K target sequence in Mycobacteria comprising a) a first amplification primer consisting of the target binding sequence of SEQ ID NO: 1 and, optionally, a non-target binding sequence for amplification of the target sequence, and (b) a second amplification primer consisting of the target binding sequence of SEQ ID NO: 2 and, optionally the non-target binding sequence for amplification of the target sequence.

2. The set of oligonucleotides of claim 1 wherein the first amplification primer consists of SEQ ID NO: 1 and the second amplification primer consists of SEQ ID NO: 2.

3. The set of oligonucleotides of claim 1 further comprising a first bumper primer consisting of SEQ ID NO: 3 and a second bumper primer consisting of SEQ ID NO: 4.

4. The set of oligonucleotides of claim 1 further comprising an assay probe for detection or identification of the target sequence.

5. The set of oligonucleotides of claim 4 wherein the assay probe is selected from the group consisting of SEQ ID NO: 9, SEQ ID NO: 10, SEQ ID NO: 11, SEQ ID NO: 7, SEQ ID NO: 8 and SEQ ID NO: 6.

6. A method for detecting a DNA K target sequence in Mycobacteria comprising:

a) amplifying the DNA K target sequence using (i) a first amplification primer consisting of the target binding sequence of SEQ ID NO: 1 and, optionally, a non-target binding sequence for amplification of the target sequence, and (ii) a second amplification primer consisting of the target binding sequence of SEQ ID NO: 2 and, optionally, the non-target binding sequence for amplification of the target sequence, and;

b) detecting the amplified DNA K target sequence using an assay probe.

7. The method of claim 6 wherein detection of the amplified DNA K target sequence is species-specific or complex-specific.

8. The method of claim 7 wherein non-specific cross-hybridization of the assay probe is reduced using a blocking oligonucleotide.

9. The method of claim 7 wherein a DNA K target sequence of a species of the M. avium complex is detected.

10. The method of claim 9 wherein the DNA K target sequence is detected using (i) a detector probe selected from the group consisting of SEQ ID NO: 7 and SEQ ID NO: 8, (ii) a capture probe consisting of SEQ ID NO: 6, and (iii) a blocking oligonucleotide selected from the group consisting of SEQ ID NO: 9, SEQ ID NO: 10 and SEQ ID NO: 11.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
( A ) LENGTH: 37 base pairs
( B ) TYPE: nucleic acid
( C ) STRANDEDNESS: single ( D ) TOPOLOGY: linear ( i i ) MOLECULE TYPE: DNA (genomic)

( x i ) SEQUENCE DESCRIPTION: SEQ ID NO:1:

TTGAATAGTC TCTTACAAGT TGACTGCAGA TCCAGGT                                37

( 2 ) INFORMATION FOR SEQ ID NO:2:

( i ) SEQUENCE CHARACTERISTICS:
                ( A ) LENGTH: 37 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:2:

TTGTTGTAAG AGACTATTGT TGACGCAGCT TGTTGTG                                37

( 2 ) INFORMATION FOR SEQ ID NO:3:

( i ) SEQUENCE CHARACTERISTICS:
                ( A ) LENGTH: 13 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:3:

GCCGACGACA ACC                                                          13

( 2 ) INFORMATION FOR SEQ ID NO:4:

( i ) SEQUENCE CHARACTERISTICS:
                ( A ) LENGTH: 13 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:4:

CGGTCAGCTC GAA                                                          13

( 2 ) INFORMATION FOR SEQ ID NO:5:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:5:

GTACCAGGGT GAGCG                                                        15

( 2 ) INFORMATION FOR SEQ ID NO:6:

( i ) SEQUENCE CHARACTERISTICS:
                ( A ) LENGTH: 14 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:6:

GTACCAGGGT GAGC  14

( 2 ) INFORMATION FOR SEQ ID NO:7:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:7:

CGAAATCGCC GCG  13

( 2 ) INFORMATION FOR SEQ ID NO:8:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:8:

GAAATCGCTT CGCA  14

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:9:

GTATCAGGGT GAGC  14

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:10:

GTATCAGGGT GAGCG  15

( 2 ) INFORMATION FOR SEQ ID NO:11:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:11:

TATCAGGGTG AGCG  14

( 2 ) INFORMATION FOR SEQ ID NO:12:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

GACGCAGCGG GCGCGGCGAC GCGCCACCCG GACACCGGAC GCAGCAAAAA  50

( 2 ) INFORMATION FOR SEQ ID NO:13:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

GACGCAGCGG GCGAAGCGAC GCGCCACCCG GACACCGGAC GCAGCAAAAA  50

( 2 ) INFORMATION FOR SEQ ID NO:14:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

GACGCAGCGG GCGAAGCGAC GCGCCACCCG AACACCGGAC GCAGCAAAAA  50

( 2 ) INFORMATION FOR SEQ ID NO:15:

( i ) SEQUENCE CHARACTERISTICS:
( A ) LENGTH: 439 base pairs
( B ) TYPE: nucleic acid
( C ) STRANDEDNESS: single
( D ) TOPOLOGY: linear ( v i ) ORIGINAL SOURCE:
( A ) ORGANISM: Mycobacterium paratuberculosis ( x i ) SEQUENCE DESCRIPTION: SEQ ID NO:15:

AAGGGTGGCG TGATGACCAA GCTGATCGAA CGCAACACCA CCATCCCGAC CAAGCGGTCC  60

GAGACGTTCA CCACGGCCGA CGACAACCAG CCGTCGGTGC AGATCCAGGT GTATCAGGGT  120

GAGCGCGAAA TCGCCGCGCA CAACAAGCTG CTCGGCTCCT TCGAGCTGAC CGGAATTCCG  180

CCGGCGCCCC GCGGCGTGCC GCAGATCGAG GTCACCTTCG ACATCGACGC CAACGGCATC  240

GTGCACGTCA CCGCCAAGGA CAAGGGCACC GGTAAGGAGA ACACGATCAA GATCCAGGAG  300

GGCTCCGGCC TGTCCAAGGA GGAGATCGAC CGGATGATCA AGGACGCCGA GGCGCACGCC  360

GAGGAGGACC GCAAGAGGCG CGAGGAAGCC GACGTCCGCA ACCAAGCGGA ATCGCTTGTC  420

TACCAGACGG AGAAGTTCG  439

( 2 ) INFORMATION FOR SEQ ID NO:16:

( i ) SEQUENCE CHARACTERISTICS:
( A ) LENGTH: 439 base pairs
( B ) TYPE: nucleic acid
( C ) STRANDEDNESS: single ( D ) TOPOLOGY: linear ( v i ) ORIGINAL SOURCE:
    ( A ) ORGANISM: Mycobacterium avium ( x i ) SEQUENCE DESCRIPTION: SEQ ID NO:16:

| | | | | | |
|---|---|---|---|---|---|
| AAGGGTGGCG | TGATGACCAA | GCTGATCGAA | CGCAACACCA | CCATCCCGAC | CAAGCGGTCC | 60
| GAGACGTTCA | CCCCGGCCGA | CGACAACCAG | CCGTCGGTGC | AGATCCAGGT | GTACCAGGGT | 120
| GAGCGCGAAA | TCGCCGCGCA | CAACAAGCTG | CTCGGCTCCT | TCGAGCTGAC | CGGAATCCCG | 180
| CCGGCGCCCC | GCGGCGTGCC | GCAGATCGAG | GTCACCTTCG | ACATCGACGC | CAACGGCATC | 240
| GTGCACGTCA | CCGCGAAGGA | CAAGGGCACC | GGTAAGGAGA | ACACGATCAA | GATCCAGGAG | 300
| GGCTCCGGCC | TGTCCAAGGA | GGAGATCGAC | CGGATGATCA | AGGACGCCGA | GGCGCACGCC | 360
| GAGGAGGACC | GCAAGCGGCG | CGAGGAAGCC | GACGTCCGCA | ACCAAGCGGA | ATCGCTTGTC | 420
| TACCAGACGG | AGAAGTTCG | | | | | 439

( 2 ) INFORMATION FOR SEQ ID NO:17:

( i ) SEQUENCE CHARACTERISTICS:
        ( A ) LENGTH: 439 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium intracellulare     ( x i ) SEQUENCE DESCRIPTION: SEQ ID NO:17:

| | | | | | |
|---|---|---|---|---|---|
| AAGGGTGGCG | TGATGACCAA | GCTCATCGAG | CGCAACACCA | CGATCCCGAC | CAAGCGGTCG | 60
| GAGACCTTCA | CCACGGCCGA | TGACAACCAG | CCGTCGGTGC | AGATCCAGGT | GTACCAGGGT | 120
| GAGCGCGAAA | TCGCTTCGCA | CAACAAGCTG | CTCGGCTCCT | TCGAGCTGAC | CGGCATCCCG | 180
| CCGGCGCCCC | GCGGCGTCCC | GCAGATCGAG | GTCACCTTCG | ACATCGACGC | CAACGGCATC | 240
| GTGCACGTCA | CGGCCAAGGA | CAAGGGCACC | GGCAAGGAGA | ACACGATCAA | AATCCAGGAG | 300
| GGCTCCGGCC | TGTCCAAGGA | GGAGATCGAC | CGGATGATCA | AGGACGCCGA | GGCGCACGCC | 360
| GAGGAGGACC | GCCAGCGTCG | CGAGGAGGCC | GACGTCCGCA | ACCAGGCCGA | ATCGCTGGTC | 420
| TACCAGACGG | AGAAGTTCG | | | | | 439

( 2 ) INFORMATION FOR SEQ ID NO:18:

( i ) SEQUENCE CHARACTERISTICS:
        ( A ) LENGTH: 349 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium scrofulaceum     ( x i ) SEQUENCE DESCRIPTION: SEQ ID NO:18:

| | | | | | |
|---|---|---|---|---|---|
| CCGTCGGTGC | AGATCCAGGT | CTATCAGGGT | GAGCGCGAAA | TCGCTTCGCA | CAACAAGCTG | 60
| CTCGGCTCCT | TCGAGCTGAC | CGGCATCCCG | CCGGCCCCGC | GCGGCGTGCC | CCAGATCGAG | 120
| GTCACCTTCG | ACATCGACGC | CAACGGCATC | GTGCACGTCA | CGGCCAAGGA | CAAGGGCACC | 180
| GGCAAGGAGA | ACACGATCAA | GATCCAGCAG | GGCTCCGGCC | TGTCCAAGGA | GGAGATCGAC | 240
| CGGATGATCA | AGGACGCCGA | GGCGCACGCC | GAGGAGGACC | GCCAGCGTCG | CGAGGAGGCC | 300
| GACATCCGCA | ACCAGGCCGA | GTCGCTGGTC | TACCAGACGG | AGAAGTTCG | | 349

( 2 ) INFORMATION FOR SEQ ID NO:19:

( i ) SEQUENCE CHARACTERISTICS:
        ( A ) LENGTH: 439 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium chelonae     ( x i ) SEQUENCE DESCRIPTION: SEQ ID NO:19:

```
AAGGGTGGCG TGATGACCAA GCTCATCGAG CGCAACACCA CCATCCCCAC CAAGCGGTCT      60
GAGACGTTCA CCACCGCGGA CGACAACCAG CCGTCGGTGC AGATCCAGGT GTATCAGGGT     120
GAGCGCGAAA TCGCTTCGCA CAACAAGCTC CTGGGCTCCT TCGAGCTGAC CGGAATTCCG     180
CCGGCCCCGC GCGGTGTGCC GCAGATCGAG GTCACCTTCG ACATCGATGC GAACGGCATC     240
GTGCACGTGA CCGCGAAGGA CAAGGGCACC GGCAAGGAGA ACACGATCAA GATCCAGGAA     300
GGCTCCGGCC TGTCCAAGGA AGAGATCGAC CGGATGATCA AGGACGCCGA GGCGCACGCC     360
GACGAGGACA AGAAGCGCCG CGAAGAGGCC GATGTCCGTA ACCAGGCCGA GTCGCTGGTC     420
TACCAGACGG AGAAGTTCA                                                  439
```

( 2 ) INFORMATION FOR SEQ ID NO:20:

( i ) SEQUENCE CHARACTERISTICS:
        ( A ) LENGTH: 439 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium chelonae (a)

( x i ) SEQUENCE DESCRIPTION: SEQ ID NO:20:

```
AAGGGTGGCG TGATGACCAA GCTCATCGAG CGCAACTCCA CCATCCCCCC CGAGCGGTCT      60
GAGACGTTCA CCTCCTCGGA CGTCAACCAG CCGTCGGTGC AGATCCAGGT GTATCGGGGT     120
GAGCGCGAAW TCGCTTCGCA CAACAAGCTC CTGGGCTCCT TCGAGCTGAC CGGAATTCCG     180
CCGGCCCCGC GCGGTGTGCC GCAGATCGAG GTCACCTTCG ACATCGATGC GAACGGYATC     240
GTGCACGTGA CCGCGAAGGA CAAGGGCACC GGCAAGGAGA ACACGATCAA GATCCAGGAA     300
GGCTCCGGCC TGTCCAAGGA AGAGATCGAC CGGATGATCA AGGACGCCGA GGCGCACGCC     360
GACGAGGACA AGAAGCGCCG CGAAGAGGNC GATGTCCGTA ACCAGGCCGA GTCGNTGGTC     420
TACCAGAAGG AGAAGTTCA                                                  439
```

( 2 ) INFORMATION FOR SEQ ID NO:21:

( i ) SEQUENCE CHARACTERISTICS:
        ( A ) LENGTH: 439 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium tuberculosis     ( x i ) SEQUENCE DESCRIPTION: SEQ ID NO:21:

```
AAGGGCGGGG TGATGACCAG GCTCATCGAG CGCAACACCA CGATCCCCAC CAAGCGGTCG      60
GAGACTTTCA CCACCGCCGA CGACAACCAA CCGTCGGTGC AGATCCAGGT CTATCAGGGG     120
GAGCGTGAGA TCGCCGCGCA CAACAAGTTG CTCGGGTCCT TCGAGCTGAC CGGCATCCCG     180
CCGGCGCCGC GGGGGATTCC GCAGATCGAG GTCACTTTCG ACATCGACGC CAACGGCATT     240
```

```
GTGCACGTCA  CCGCCAAGGA  CAAGGGCACC  GGCAAGGAGA  ACACGATCCG  AATCCAGGAA      300

GGCTCGGGCC  TGTCCAAGGA  AGACATTGAC  CGCATGATCA  AGGACGCCGA  AGCGCACGCC      360

GAGGAGGATC  GCAAGCGTCG  CGAGGAGGCC  GATGTTCGTA  ATCAAGCCGA  GACATTGGTC      420

TACCAGACGG  AGAAGTTCG                                                       439
```

( 2 ) INFORMATION FOR SEQ ID NO:22:

( i ) SEQUENCE CHARACTERISTICS:
        ( A ) LENGTH: 439 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium africanum     ( x i ) SEQUENCE DESCRIPTION: SEQ ID NO:22:

```
AAGGGCGGGG  TGATGACCAG  GCTCATCGAG  CGCAACACCA  CGATCCCCAC  CAAGCGGTCG       60

GAGACTTTCA  CCACCGCCGA  CGACAACCAA  CCGTAGGTGC  AGATCCAGGT  CTATCAGGGG      120

GAGCGTGAGA  TCGCCGCGCA  CAACAAGTTG  CTCGGGTCCT  TCGAGCTGAC  CGGCATCCCG      180

CCGGCGCCGC  GGGGATTCC   GCAGATCGAG  GTCACTTTCG  ACATCGACGC  CAACGGCATT      240

GTGCACGTCA  CCGCCAAGGA  CAAGGGCACC  GGCAAGGAGA  ACACGATCCG  AATCCAGGAA      300

GGCTCGGGCC  TGTCCAAGGA  AGACATTGAC  CGCATGATCA  AGGACGCCGA  AGCGCACGCC      360

GAGGAGGATC  GCAAGCGTCG  CGAGGAGGCC  GATGTCCGTA  ATCAAGCCGA  GTCGCTGGTC      420

TACCAGACGG  AGAAGTTCG                                                       439
```

( 2 ) INFORMATION FOR SEQ ID NO:23:

( i ) SEQUENCE CHARACTERISTICS:
        ( A ) LENGTH: 349 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium bovis BCG     ( x i ) SEQUENCE DESCRIPTION: SEQ ID NO:23:

```
CCGTCGGTGC  AGATCCAGGT  CTATCAGGGG  GAGCGTGAGA  TCGCCGCGCA  CAACAAGTTG       60

CTCGGGTCCT  TCGAGCTGAC  CGGCATCCCG  CCGGCGCCGC  GGGGATTCC   GCAGATCGAG      120

GTCACTTTCG  ACATCGACGC  CAACGGCATT  GTGCACGTCA  CCGCCAAGGA  CAAGGGCACC      180

GGCAAGGAGA  ACACGATCCG  AATCCAGGAA  GGCTCGGGCC  TGTCCAAGGA  AGACATTGAC      240

CGCATGATCA  AGGACGCCGA  AGCGCACGCC  GAGGAGGATC  GCAAGCGTCG  CGAGGAGGCC      300

GATGTTCGTA  ATCAAGCCGA  GACATTGGTC  TACCAGACGG  AGAAGTTCG                   349
```

( 2 ) INFORMATION FOR SEQ ID NO:24:

( i ) SEQUENCE CHARACTERISTICS:
        ( A ) LENGTH: 349 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium bovis     ( x i ) SEQUENCE DESCRIPTION: SEQ ID NO:24:

```
CCGTCGGTGC  AGATCCAGGT  CTATCAGGGG  GAGCGTGAGA  TCGCCGCGCA  CAACAAGTTG       60
```

```
CTCGGGTCCT  TCGAGCTGAC  CGGCATCCCG  CCGGCGCCGC  GGGGGATTCC  GCAGATCGAG    120

GTCACTTTCG  ACATCGACGC  CAACGGCATT  GTGCACGTCA  CCGCCAAGGA  CAAGGGCACC    180

GGCAAGGAGA  ACACGATCCG  AATCCAGGAA  GGCTCGGGCC  TGTCCAAGGA  AGACATTGAC    240

CGCATGATCA  AGGACGCCGA  AGCGCACGCC  GAGGAGGATC  GCAAGCGTCG  CGAGGAGGCC    300

GATGTTCGTA  ATCAAGCCGA  GACATTGGTC  TACCAGACGG  AGAAGTTCG                349
```

( 2 ) INFORMATION FOR SEQ ID NO:25:

( i ) SEQUENCE CHARACTERISTICS:
        ( A ) LENGTH: 439 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium gordonae     ( x i ) SEQUENCE DESCRIPTION: SEQ ID NO:25:

```
AAGGGCGGCG  TGATGACCAA  GCTCATCGAG  CGCAACACCA  CCATCCCGAC  CAAGCGGTCG    60

GAGACCTTCA  CCACGGCCGA  CGACAACCAG  CCGTCGGTGC  AGATCCAGGT  CTACCAGGGT    120

GAGCGTGAGA  TCGCCTCGGC  CAACAAGCTG  CTCGGCAGCT  TCGAGTTGAC  CGGTATCGCC    180

CCGGCTCCGC  GCGGGGTGCC  CCAGATCGAG  GTCACCTTTG  ACATCGACGC  CAACGGCATC    240

GTGCACGTCA  CGGCCAAGGA  CAAGGGCACC  GGCAAGGAGA  ACACGATCCG  TATCCAGGAG    300

GGCTCCGGCA  TCTCCAAGGA  AGAGATCGAC  CGGATGATCA  AGGAGGCCGA  AGCGCACGCG    360

GACGAGGACC  GCAAGCGTCG  CGAGGAGGCC  GACGTTCGCA  ACCAGGCCGA  GACGCTGGTC    420

TACCAGACGG  AGAAGTTCG                                                    439
```

( 2 ) INFORMATION FOR SEQ ID NO:26:

( i ) SEQUENCE CHARACTERISTICS:
        ( A ) LENGTH: 349 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium fortuitum     ( x i ) SEQUENCE DESCRIPTION: SEQ ID NO:26:

```
CCGTCGGTGC  AGATCCAGGT  CTTCCAGGGT  GAGCGCGAAA  TCGCTTCTCA  CAACAAGCTG    60

CTCGGCTCCT  TCGAGCTGAC  CGGCATCCCG  CCGGCCCGC   GTGGCGTGCC  GCAGATCGAG    120

GTCACCTTCG  ACATCGACGC  CAACGGCATC  GTGCACGTGA  CCGCCAAGGA  CAAGGGCACC    180

GGCAAGGAAA  ACACGATCAA  GATCCAGGAA  GGCTCCGGCC  TGTCCAAGGA  AGAGATCGAC    240

CGGATGATCA  AGGACGCCGA  GGCACGCACC  GAAGAGGACA  GAAGCGTCG   CGAAGAGGCC    300

GACGTCCGCA  ACCAAGCCGA  GTCGCTGGTC  TACCAGACGG  AGAAGTTCG               349
```

( 2 ) INFORMATION FOR SEQ ID NO:27:

( i ) SEQUENCE CHARACTERISTICS:
        ( A ) LENGTH: 439 base pairs
        ( B ) TYPE: nucleic acid
        ( C ) STRANDEDNESS: single
        ( D ) TOPOLOGY: linear     ( v i ) ORIGINAL SOURCE:
        ( A ) ORGANISM: Mycobacterium kansasii     ( x i ) SEQUENCE DESCRIPTION: SEQ ID NO:27:

-continued

| | | | | | |
|---|---|---|---|---|---|
|AAGGGCGGCG|TGATGACCAA|GCTGATCGAG|CGCAACGCCA|CGATCCCGAC|CAAGCGGTCG| 60
|GAGACCTTCA|CCACCGCCGA|CGACAACCAG|CCGTCGGTGC|AGATCCAGGT|CTATCAGGGT| 120
|GAGCGCGAGA|TCGCCTCGCA|CAACAAGCTG|CTCGGCTCCT|TCGAGCTGAC|CGGCATCCCG| 180
|CCGGCGCCCC|GCGGCGTCCC|GCAGATCGAG|GTCACCTTCG|ACATCGACGC|CAACGGCATC| 240
|GTGCATGTCA|CGGCCAAGGA|CAAGGGCACC|GGCAAGGAGA|ACACCATCCG|GATCCAGGAA| 300
|GGCTCGGGCC|TGTCCAAGGA|AGAGATCGAC|CGGATGATCA|AGGAYGCCGA|GGCGCACGCC| 360
|GAGGAGGACC|GCAAGCGTCG|CGAGGAGGCC|GACGTCCGCA|ACCAGGCCGA|GACGCTGGTC| 420
|TACCAGACGG|AGAAGTTCG| | | | | 439

(2) INFORMATION FOR SEQ ID NO:28:

(i) SEQUENCE CHARACTERISTICS:
    (A) LENGTH: 439 base pairs
    (B) TYPE: nucleic acid
    (C) STRANDEDNESS: single
    (D) TOPOLOGY: linear (vi) ORIGINAL SOURCE:
    (A) ORGANISM: Rhodococcus rhodochrous (xi) SEQUENCE DESCRIPTION: SEQ ID NO:28:

| | | | | | |
|---|---|---|---|---|---|
|AAGGGCGGCG|TGATGACCAA|GCTCATCGAG|CGCAACACGA|CCATCCCCAC|CAAGCGGTCC| 60
|GAGACCTTCA|CCACGGCCGA|CGACAAAAAA|CCGTCCGTGC|AGATCCAGGT|CTACCAGGGC| 120
|GAGCGTGAGA|TCGCGGCGCA|CAACAAGCTG|CTCGGTTCGT|TCGAGCTCGG|CGGCATCGCG| 180
|CCGGCTCCGC|GCGGTGTCCC|GCAGATCGAG|GTGGCCTTCG|GCATCGACGC|CAACGGCATC| 240
|GTCCACGTCA|CCGCCCGCGA|CAAGGGCACC|GGCAAGGAGA|ACACGATCAA|GATCCAGGAA| 300
|GGCTCCGGCC|TCTCCCAGGA|GGAGATCGAT|CGGATGGTCA|AGGACGCCGA|GGTCCACGCC| 360
|GAGGAGGACC|GCAAGCGTCG|CGAGGAGGCC|GAGGTCCGCA|ACCAGGCCGA|GTCGCTCGTG| 420
|CACCAGACCG|AGAAGTTCA| | | | | 439